(12) United States Patent
Finkbeiner

(10) Patent No.: US 6,291,652 B1
(45) Date of Patent: Sep. 18, 2001

(54) ANTIBODIES SPECIFIC FOR PROTEINS HAVING POLYGLUTAMINE EXPANSIONS

(75) Inventor: Steven Finkbeiner, San Francisco, CA (US)

(73) Assignee: The Regents of the University of California, Berkeley, CA (US)

(*) Notice: Subject to any disclaimer, the term of this patent is extended or adjusted under 35 U.S.C. 154(b) by 0 days.

(21) Appl. No.: 09/478,960

(22) Filed: Jan. 7, 2000

(51) Int. Cl.$^7$ .................................................. C07K 16/00
(52) U.S. Cl. ..................... 530/388.1; 424/130.1; 424/141.1; 435/326; 435/331; 530/350; 530/388.85; 530/389.1
(58) Field of Search .................... 435/326, 331; 530/350, 388.1, 389.1, 380.85; 424/130.1, 141.1

(56) References Cited

FOREIGN PATENT DOCUMENTS

WO 97/17445    5/1997 (WO).

OTHER PUBLICATIONS

Johansson et al. Liver cell uptake and degradation of soluble immunoglobulin G immune complexes in vivo and in vitro in rats. Hepatology. vol. 24 (1996) pp. 169–175.*

Jones et al. Antibodies for targeted gene therapy: extracellular gene targeting and intracellular expression. Advanced Drug Delivery Reviews. vol. 31 (1998) pp. 153–170.*

Saragovi et al. Design and synthesis of a mimetic from an antibody complementary–determining region. Science. vol. 253 (1991) pp. 792–795.*

Scherzinger et al. Huntingtin–encoded polyglutamine expansions form amyloid–like protein aggregates in vitro and in vivo. Cell. vol. 90 (1997) pp. 549–558.*

Heiser et al. (2000) "Inhibition of huntingtin fibrillogenesis by specific antibodies and small molecules: Implications for Huntington's disease therapy." PNAS, vol. 97(12):6739–6744.

Persichetti et al. (1996) "Differential Expression of Normal and Mutant Huntington's Disease Gene Alleles." Neurobiology of Disease, vol. 3:183–190.

Imbert, et al., "Cloning of the Gene for Spinocerebellar Ataxia 2 Reveals a Locus With High Sensitivity to Expanded CAG/glutamine Repeats", Nat.Genet (Nov. 1996) 14:285–291.

Lunkes, et al., "Properties of Polyglutamine Expansion in Vitro and in Cellular Model for Huntington's Disease", Phil. Trans. R. Soc.Lond. B (1999) 354:1013–1019.

Persichetti, et al., "Mutant Huntingtin Forms in Vivo Complexes With Distinct Context–Dependent Conformatons of the Polyglutamine Segment", Neurobiology of Disease (1999) 6:364–375.

Stevanin,et al., "Screening for Proteins With Polyglutamine Expansions in Autiosomal Dominant Cerebellar Ataxias", Hum. Mol. Genet. (Dec. 1996) 5:887–1892.

Takeuchi,et al., "Molecular Cloning and Expression of a Novel Human cDNA Containing CAG Repeats", Gene(1997) 204:71–77.

Trottier,et al., "Cellular Localization of the Huntington's Disease Protein and Dicrimination of the Normal and Mutated Form", Nature Genetics (May 1995) 10:104–110.

Trorrier, et al., "Polyglutamine Expansion as a Pathological Epitope in Huntington's Disease and Four Dominant Cerebellar Ataxias", Nature Genet. (Nov. 1995) pp. 403–406.

* cited by examiner

*Primary Examiner*—Jeffrey Stucker
*Assistant Examiner*—Ulrike Winkler
(74) *Attorney, Agent, or Firm*—Bret E. Field; Bozicevic, Field & Francis

(57) ABSTRACT

Antibodies, as well as binding fragments and mimetics thereof, that specifically bind to polyglutamine expansion containing proteins, e.g. mutant huntingtin protein, are provided. The subject binding agents, e.g. antibodies, fragments and mimetics thereof, etc., are characterized in that they bind to the target polyglutamine expansion containing protein in a manner that differs from the 1C2 antibody, e.g. in terms of affinity, avidity, and the like. Also provided are methods of screening compounds for polyglutamine expansion protein binding modulation activity, as well as pharmaceutical compositions of such agents. In addition, methods and devices for screening samples for the presence of polyglutamine expansion containing proteins, e.g. mutant huntingtin protein, are provided. Finally, nucleic acids encoding the subject antibodies and methods for their expression, including in therapeutic treatment protocols, are provided.

22 Claims, No Drawings

ANTIBODIES SPECIFIC FOR PROTEINS HAVING POLYGLUTAMINE EXPANSIONS

ACKNOWLEDGEMENT OF GOVERNMENT SUPPORT

This invention was made with Government support under Grant No. NS01817, awarded by the National Institutes of Health. The Government has certain rights in this invention.

INTRODUCTION

1. Field of the Invention

The field of this invention is Huntington's disease.

2. Background of the Invention

Huntington's Disease (HD) is a devastating neurological disease which usually presents in mid adult life and results in psychiatric disturbance, involuntary movement disorder, and cognitive decline associated with inexorable progression to death, typically 17 years following onset. HD is a progressive neurodegenerative disease striking principally medium spiny GABAergic neurons of the caudate nucleus of the basal ganglia. It affects about one in 10,000 individuals and is transmitted in an autosomal dominant fashion.

HD is associated with expansion of a CAG repeat within the HD gene. The HD gene is ubiquitously expressed and conserved across a wide range of species. The HD gene encompasses 67 exons, spans over 200 kb and is associated with two transcripts of 10.3 kb and 13.6 kb, differing with respect to their 3' untranslated regions. Both messages are predicted to encode a 348 kilodalton protein containing 3144 amino acids. In addition, the HD gene encompasses a highly polymorphic CAG repeat which varies in number from 8 to 35 in normal individuals. CAG expansion beyond 36 CAG repeats is seen in persons with HD.

The increase in size of the CAG repeat in persons with HD shows a highly significant correlation with age of onset of clinical features. This association is particularly striking for persons with juvenile onset HD who have very significant expansion, usually beyond 50 repeats. The CAG repeat length in HD families does exhibit some instability that is particularly marked when children inherit the HD gene from affected fathers.

HD is one of an increasing number of disorders associated with trinucleotide repeat expansion, including myotonic dystrophy, fragile X syndrome, spinobulbar muscular atrophy (SBMA) and more recently spinocerebellar ataxia type 1 and X linked mental retardation. The common occurrence of the expanded trinucleotide repeat in each of these disorders suggests a common feature underlying their pathogenesis. There are however, still few clues as to how repeat expansion actually causes these illnesses.

As such, there is continued interest in the elucidation of underlying mechanisms of HD and similar diseases characterized by the presence of trinucleotide repeat expansions, such as polyglutamine expansions. Of use to these endeavors would be a highly specific antibody that specifically recognized mutant forms of proteins having polyglutamine expansions and did not appreciably bind to non-mutant proteins having such expansions.

Relevant Literature The 1C2 antibody is described in WO 97/17445. Also of interest are: Imbert et al., Nat. Genet. (November 1996) 14:285–291; Jones et al., J. Inherit. Metab. Dis. (June 1997) 20:125–138; Jou et al., Hum. Mol. Genet. (March 1995) 4:465–469; Li et al., Hum. Mol. Genet. (May 1998) 7:777–782; Li et al., Nature (November 1995) 378:398–402; Lunkes et al., Philos. Trans. R. Soc. Lund B. Biol. Sci. (June 1999) 354:1013–1019; Lunkes et al., Essays Biochem. (1998) 33:149–163; Takeuchi et al., Gene (December 1997) 204:71–77; Stevanin et al., Hum. Mol. Genet. (December 1996) 5:1887–1892; Trottier et al., Nature (November 1995) 378:403–406; Trottier et al., Nature Genet. (May 1995) 10:104–110; and Walling et al., J. Neurosci Res (November 1998) 54:301–308.

Intrabodies are described in U.S. Pat. Nos. 5,851,829 and 5,965,371. See also Ohage et al., J. Mol. Biol. (September 1999)291:1129–1134; Ohage et al., J. Mol. Biol. (September 1999) 291:1119–1128; and Chen et al., Hum. Gene Ther. (May 1994) 5:595–601.

SUMMARY OF THE INVENTION

Antibodies, as well as binding fragments and mimetics thereof (including intrabodies), that specifically bind to polyglutamine expansion containing proteins, e.g. mutant huntingtin protein, are provided. The subject binding agents, e.g. antibodies, fragments and mimetics thereof, etc., are characterized in that they bind to the polyglutamine expansion containing protein in a manner that differs from the 1C2 antibody, e.g. in terms of specificity, affinity, avidity, and the like. Also provided are methods of screening compounds for polyglutamine expansion protein binding modulation activity, as well as pharmaceutical compositions of such agents. In addition, methods and devices for screening samples for the presence of polyglutamine expansion containing proteins, e.g. mutant huntingtin protein, are provided. Finally, nucleic acids encoding the subject antibodies and methods for their expression, including in therapeutic treatment protocols, are provided.

DESCRIPTION OF THE SPECIFIC EMBODIMENTS

Antibodies, as well as binding fragments and mimetics thereof (including intrabodies), that specifically bind to polyglutamine expansion containing proteins, e.g. mutant huntingtin protein, are provided. The subject binding agents, e.g. antibodies, fragments and mimetics thereof, etc., are characterized in that they bind to the polyglutamine expansion containing protein in a manner that differs from the 1C2 antibody, e.g. in terms of at least one of specificity, affinity and avidity. Also provided are methods of screening compounds for polyglutamine expansion protein binding modulation activity, as well as pharmaceutical compositions of such agents. In addition, methods and devices for screening samples for the presence of polyglutamine expansion containing proteins, e.g. mutant huntingtin protein, are provided. Finally, nucleic acids encoding the subject antibodies and methods for their expression, including in therapeutic treatment protocols, are provided.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

ANTIBODIES

As summarized above, antibodies that recognize proteins having polyglutamine expansions are provided. More specifically, antibody compositions containing one or more antibodies, usually a plurality of antibodies and more usually a large plurality of antibodies, which recognize proteins having polyglutamine expansions are provided. By "recognize" is meant that the antibodies bind to proteins having polyglutamine expansions. The subject antibodies are specific for proteins having polyglutamine expansions. As the subject antibodies are specific for proteins having polyglutamine expansions, they bind preferentially to polyglutamine expansion containing proteins, as compared to proteins that do not contain polyglutamine expansions. In many embodiments, the subject antibodies do not bind to any appreciable extent to proteins that do not contain a polyglutamine expansion.

The polyglutamine expansions of the proteins to which the antibodies of the subject invention bind are glutamine stretches of at least 35 glutamine residues, where the number of glutamine residues in the polyglutamine expansion domain of the proteins typically ranges from about 35 to 200, usually from about 35 to 175 and more usually from about 35 to 150. The polyglutamine expansion of the target protein may be a heteropolymer stretch or homopolymeric stretch. Where the polyglutamine expansion is a heteropolyglutamine expansion, the number of non-glutamine residues in the expansion is limited, where the number % of non-glutamine residues does not exceed about 10, usually does not exceed about 5 and more usually does not exceed about 3. In many embodiments, the polyglutamine expansion is a homopolyglutamine expansion, by which is meant that the polyglutamine expansion does not include any non-glutamine residues.

Generally, the polyglutamine expansion containing proteins recognized by the subject antibodies are proteins associated with disease conditions. Polyglutamine expansion containing proteins of interest that are associated with disease conditions include: mutant huntingtin protein, mutant androgen receptor and the like. The subject antibodies specifically recognize mutant huntingtin protein having a polyglutamine expansion of at least 35 residues in length, where the polyglutamine expansion typically ranges from about 35 to 200, usually from about 35 to 175 and more usually from about 35 to 150. As such, one embodiment of the subject invention provides antibodies that specifically recognize mutant huntingtin protein whose presence is associated with Huntington's disease.

The subject antibodies are further characterized in that they differ from the 1C2 antibody with respect to at least one of specificity, affinity and avidity for their target polyglutamine expansion containing protein, e.g. a mutant huntingtin protein having a polyglutamine expansion longer than about 35 glutamine residues in length. The 1C2 antibody is described in WO 97/17445. As the specificity of the subject antibodies differs from that of the 1C2 antibody, the subject antibodies do not bind to all of the same proteins to which the 1C2 antibody binds. For example, the 1C2 antibodies binds to the transcription factor, TATA-binding protein (TBP), in addition to mutant huntingtin protein, i.e. the 1C2 antibody cross-reacts with TBP as well as mutant huntingtin protein. In comparison to 1C2, the subject antibodies bind less with TBP, where the degree of decreased binding is at least about 2 fold, usually at least about 5 fold and more usually at least about 10 fold. As such, the specificity of the subject antibodies differs from the specificity of 1C2. In certain embodiments, the affinity of the subject antibodies for the target polyglutamine expansion containing protein, e.g. mutant huntingtin protein, differs from the affinity of 1C2 for the same protein, where the magnitude of the difference is typically at least about 2 fold, usually at least about 5 fold and more usually at least about 10 fold. The affinity of the subject antibodies for the polyglutamine expansion containing protein to which they specifically bind ranges from about $10^7$ to $10^9$ l/m usually from about $10^8$ to $10^9$ l/m. In certain embodiments, the avidity of the subject antibodies for a polyglutamine expansion containing protein differs from the avidity of the 1C2 antibody for the same protein. In these embodiments, the magnitude of the difference is typically at least about 2 fold, usually at least about 5 fold and more usually at least about 10 fold. As such, the subject antibodies differ from the 1C2 antibody with respect to at least one of specificity, affinity and avidity.

The subject antibody compositions may be polyclonal compositions, such that a heterogeneous population of antibodies differing by specificity is present in the composition, or monoclonal compositions, in which a homogeneous population of identical antibodies that have the same specificity for the target polyglutamine expansion containing protein are present. As such, both monoclonal and polyclonal antibodies are provided by the subject invention. In many preferred embodiments, the subject antibodies are monoclonal antibodies. Specific monoclonal antibodies of interest include: 1F11E5, 4H7H7, 3A2D3, 4F1B5, 3C4A6, 3B5H10, where hybridomas that produce these specific monoclonal antibodies are deposited with the American Type Culture Collection depository (10801 University Boulevard, Manassas, Va. 20110–2209) and have been assigned ATCC accession nos. PTA-2846, PTA-2847, PTA-2849, PTA-2851, PTA-2850, and PTA-2848, respectively.

METHODS OF MAKING THE SUBJECT ANTIBODIES

The subject antibodies may be prepared using any convenient methodology. Generally, an immunogen capable of giving rise to an antibody response characterized by the presence of antibodies of the subject invention is employed. The immunogen at least includes a portion of a mutant huntingtin protein that includes a polyglutamine expansion. Of particular interest are immunogens that include a polyglutamine expansion of from about 35 to 200 residues, usually from about 35 to 150 residues. Preferably, the portion of the mutant huntingtin protein present in the immunogen is present in its native state, i.e. native conformation. In certain embodiments, other domains are also present in the immunogens. For example, a glutathione-S-transferase domain may be present in the immunogen, such as is found in the immunogen employed in the working exemplification, supra. The immunogen is employed in the preparation of the subject antibodies as follows.

For preparation of polyclonal antibodies, the first step is immunization of the host animal with the immunogen. To increase the immune response of the host animal, the immunogen may be combined with an adjuvant, where suitable adjuvants include alum, dextran, sulfate, large polymeric anions, oil & water emulsions, e.g. Freund's adjuvant, Freund's complete adjuvant, and the like. The immunogen may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The immunogen is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

As with the preparation of polyclonal antibodies, the first step in preparing monoclonal antibodies specific for the polyglutamine expansion containing proteins, such as mutant huntingtin protein, is to immunize a suitable host, where suitable hosts include rats, hamsters, mice and the like, and are preferably mice. The immunogen is administered to the host in any convenient manner, where such methods include: subcutaneous injection with adjuvants, nitrocellulose implants comprising the immunogen, intrasplenic injections, and the like, where the immunization protocol may be modulated to obtain a desired type of antibody, e.g. IgG or IgM, where such methods are known in the art. Following immunization, plasma cells are harvested from the immunized host, where sources of plasma cells include the spleen, lymph nodes and the like, with the spleen being preferred. The plasma cells are then immortalized with myeloma cells to produce hybridoma cells. A variety of myeloma cell lines are available, where the myeloma cell line will preferably be HGPRT negative, incapable of producing or secreting its own antibodies, and growth stable, where specific cell lines of interest include p3U1, SP 2/0 Ag14, P3×63Ag8.653 (Dr. Greenberg, V.A. Hospital) and the like. The plasma and myeloma cells are fused by combining the cells in a fusion medium usually in a ratio of about 10 plasma cells to 1 myeloma cell, where suitable fusion mediums include a fusion agent, e.g. PEG 1000, and the like. Following fusion, the fused cells will be selected, e.g. by growing on HAT medium.

Representative hybridomas according to the subject invention include those hybridomas that secrete one of the following monoclonal antibodies: 1F11E5, 4H7H7, 3A2D3, 4F1B5, 3C4A6, 3B5H10. Specific hybridomas of interest include those having ATCC accession nos. PTA-2846, PTA-2847, PTA-2849, PTA-2851, PTA-2850, and PTA-2848.

Following hybridoma cell production, culture supernatant from individual hybridomas is screened for reactivity with mutant huntingtin protein using standard techniques, where such screening techniques include ELISA, dot blot immunoassays and the like. The antibody may be purified from the supernatants or ascites fluid by conventional techniques, e.g. affinity chromatography using mutant huntingtin protein bound to an insoluble support, protein A sepharose and the like.

BINDING FRAGMENTS AND MIMETICS

Also provided by the subject invention are binding fragments of the subject antibodies and binding mimetics thereof, where these fragments and mimetics share the binding characteristics of the subject antibodies, e.g. specificity, affinity, avidity etc. for the polyglutamine expansion protein, e.g. mutant huntingtin protein. For example, the subject antibodies may be modified in a number of different ways to optimize their utility for use in a particular immunoassay. For example, antibody fragments, such as Fv, F(abN)$_2$ and Fab may be prepared by cleavage of the intact protein, e.g. by protease or chemical cleavage.

Also of interest are recombinantly produced antibody fragments, such as single chain antibodies or scFvs, where such recombinantly produced antibody fragments retain the binding characteristics of the above antibodies. Such recombinantly produced antibody fragments generally include at least the $V_H$ and $V_L$ domains of the subject antibodies, so as to retain the binding characteristics of the subject antibodies. These recombinantly produced antibody fragments or mimetics of the subject invention may be readily prepared from the provided hybridomas of the present invention using any convenient methodology, such as the methodology disclosed in U.S. Pat. Nos. 5,851,829 and 5,965,371; the disclosures of which are herein incorporated by reference.

DIAGNOSTIC APPLICATIONS

The subject antibodies, binding fragments and mimetics thereof find use in immunoassays that are capable of providing for the detection of disease associated polyglutamine expansion containing proteins, such as mutant huntingtin protein, in a sample. In such assays, the sample suspected of comprising the polyglutamine expansion containing protein of interest will usually be obtained from a subject, such as a human subject, suspected of suffering from the disease of interest or at risk for developing the disease of interest. The sample is generally a physiological sample from the patient, where the physiological sample may be blood, tissue and the like. The sample may or may not be pretreated prior to assay.

A number of different immnunoassay formats are known in the art and may be employed in detecting the presence of protein of interest in a sample. Immunoassays of interest include Western blots on protein gels or protein spots on filters, where the antibody is labeled, as is known in the art. A variety of protein labeling schemes are known in the art and may be employed, the particular scheme and label chosen being the one most convenient for the intended use of the antibody, e.g. immunoassay. Examples of labels include labels that permit both the direct and indirect measurement of the presence of the antibody. Examples of labels that permit direct measurement of the antibody include radiolabels, such as 3H or $^{125}$I, fluorescers, dyes, beads, chemilumninescers, colloidal particles, and the like. Examples of labels which permit indirect measurement of the presence of the antibody include enzymes where a substrate may provided for a colored or fluorescent product. For example, the antibodies may be labeled with a covalently bound enzyme capable of providing a detectable product signal after addition of suitable substrate. Instead of covalently binding the enzyme to the antibody, the antibody may be modified to comprise a first member of specific binding pair which specifically binds with a second member of the specific binding pair that in conjugated to the enzyme, e.g. the antibody may be covalently bound to biotin and the enzyme conjugate to streptavidin. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Other immunoassays include those based on a competitive formats, as are known in the art. One such format would be where a solid support is coated with the polyglutamine containing protein, e.g. mutant huntingtin protein. Labeled antibody is then combined with a sample suspected of comprising protein of interest to produce a reaction mixture which, following sufficient incubation time for binding complexes to form, is contacted with the solid phase bound protein. The amount of labeled antibody which binds to the solid phase will be proportional to the amount of protein in the sample, and the presence of protein may therefore be detected. Other competitive formats that may be employed include those where the sample suspected of comprising protein is combined with a known amount of labeled protein and then contacted with a solid support coated with antibody specific for the protein. Such assay formats are known in the art and further described in both Guide to Protein Purification, supra, and Antibodies, A Laboratory Manual, supra.

In immunoassays involving solid supports, the insoluble supports may be any compositions to which antibodies or fragments thereof can be bound, which is readily separated from soluble material, and which is otherwise compatible with the overall immunoassay method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Before adding patient samples or fractions thereof, the non-specific binding sites on the insoluble support i.e. those not occupied by the first antibody, are generally blocked. Preferred blocking agents include non-interfering proteins such as bovine serum albumin, casein, gelatin, and the like. Alternatively, several detergents at non-interfering concentrations, such as Tween, NP40, TX100, and the like may be used.

It is particularly convenient in a clinical setting to perform the immunoassay in a self-contained apparatus, and such devices are provided by the subject invention. A number of such devices and methods for their use are known in the art. The apparatus will generally employ a continuous flow-path of a suitable filter or membrane, having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. The measuring region may have bound to it the first antibody, and second labeled antibody combined with the assayed sample and the sandwich assay performed as above.

SCREENING

The subject antibodies, binding fragments and mimetics thereof also find use in screening applications designed to identify agents or compounds that are capable of modulating, e.g. inhibiting, the binding interaction between the protein to which the antibody binds and a cellular target. For example, the subject antibodies find use in screening assays that identify compounds capable of modulating the interaction between mutant huntingtin protein and its cellular targets. In such assays, the subject antibody is contacted with mutant huntingtin protein in the presence of a candidate modulation agent and any resultant binding complexes between the antibody and the mutant huntingtin protein are detected. The results of the assay are then compared with a control. Those agents which change the amount of binding complexes that are produced upon contact are identified as agents that modulate the binding activity of mutant huntingtin protein and therefore are potential therapeutic agents. Of interest in many embodiments is the identification of agents that inhibit, at least to some extent, the binding of mutant huntingtin protein with its target. In many assays, at least one of the protein or antibody is attached to a solid support and at least one of these members is labeled, where supports and labels are described supra.

A variety of different candidate agents may be screened by the above screening methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

METHODS OF TREATING

Also provided are methods of treating a host suffering from a disease condition associated with the presence of a polyglutamine expansion containing protein. By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as those described in the background section, supra. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

In certain embodiments, the methods of treatment involve administration of an effective amount of a compound that modulates, e.g. inhibits, the interaction of the mutant protein containing the polyglutamine expansion, e.g. mutant huntingtin protein, with its cellular targets. "Effective amount" means a dosage sufficient to produce a desired result.

Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Of interest in many embodiments are agents that have been identified using the above described screening methods of the subject invention.

In those embodiments where an effective amount of a small molecule agent, as described above, is administered, the agent may be administered using any convenient protocol. In the subject methods, the active agent(s) may be administered to the host using any convenient means capable of resulting in the therapeutic activity. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Also provided by the subject invention are methods of treating disease conditions using intrabodies, i.e. non-secreted forms of the subject antibodies, e.g. scFv analogs of the subject antibodies, as described supra. Intrabodies and methods for their use in the treatment of disease conditions are described in U.S. Pat. Nos. 5,851,829 and 5,965,371; the disclosures of which are herein incorporated by reference. In such methods, a nucleic acid encoding the intrabody, generally in the form of an expression cassette that includes a sequence encoding the antibody domains of interest, such as the $V_H$ and $V_L$ domains, as well as other components, e.g. promoters, linkers, intracellular localization domains or sequences, etc., is introduced into the target cells in which intrabody production is desired. The nucleic acid is introduced into the target cells using any convenient methodology, e.g. through use of a vector, such as a viral vector, liposome vector, by biolistic transfection and the like, where suitable vectors are well known in the art. Following introduction of the nucleic acid into the target cells, the nucleic acid is allowed to be expressed in the target cell, whereby intrabodies that specifically bind to the protein of interest, e.g. mutant huntingtin protein, are produced in the cell. Production of the intrabodies interferes with the binding activity of the protein, e.g. mutant huntingtin protein, and thereby treats the host suffering from the disease condition.

The following examples are offered by way of illustration and not by way of limitation.

EXPERIMENTAL

I. Antibody Generation

A plasmid that encodes a glutathione-S-transferase (GST) fusion protein of an N-terminal fragment of mutant human huntingtin protein was a gift from Dr. Frederic Saudou (Curie Intitute, Paris, France). The plasmid encodes a fragment of mutant human huntingtin protein that corresponds to the first 171 amino acids of huntingtin protein and includes a homopolymeric stretch of 66 glutamines. The plasmid was transformed into *E. coli* and the expression of the GST-171-66 fragment was induced by standard methods. The bacterial culture was pelleted by centrifugation and lysed by sonication. The lysate was cleared by centrifugation and the GST-171-66 protein was batch purified using glutathione beads bound to agarose. The beads were washed several times to remove impurities and the GST-171-66 bound beads were transferred to a column for further washes. After washing, the GST-171-66 protein was eluted using excess glutahione and the eluted protein was measured by Bradford assay and analyzed by polyacrylamide gel electrophoresis (PAGE) and Coomassie staining and Western blotting. The purified immunogen was concentrated by ultrafiltration for injection and initial screening. Six mice were injected with the immunogen and two were chosen based on ELISA assays against the immunogen and their seroreactivity by Western blotting against mutant and wild-type htt expressed in COS cells. Spleens were isolated from the two mice and subjected to fusion to create hybridomas. Tissue culture supernatants from pooled parental clones were screened ELISA against GST-171-66 and by Western analysis against COS cell extracts containing wild-type and mutant hungtinton's protein. Parent clones positive by Western blotting were re-plated at monoclonal densities and mnoclonal tissue culture supernatants were further screened by Western blotting against mutant and wild-type huntingtin protein. Monclonal lines whose supernatants showed specific reactivity to mutant huntingtin were isolated and used to form ascites fluid and samples of the cell lines were frozen down for use in intrabody production.

II. Comparative Examples with 1C2

The monoclonal antibodies developed according to the protocol of Example I above, i.e. 1F11E5, 4H7H7, 3A2D3, 4F1B5, 3C4A6, 3B5H10, were all compared to the 1C2 antibody by western blot analysis and immunoprecipitation. The antibodies were screened against extracts prepared from COS cells expressing wild-type or mutant huntingtin. First, equal amounts of wild-type (480-17) and mutant huntingtin (480-68) were loaded into individual lanes of a denaturing polyacrylamide gel, subjected to electrophoresis and transferred to nitrocellulose. One lane was probed with a monoclonal antibody (4C8) that binds to a region of huntingtin that flanks the polyglutamine stretch and therefore is capable of binding both wild-type and mutant huntingtin. The signal produced with the 4C8 antibody confirmed that we had approximately equal amounts of wild-type and mutant huntingtin on the nitrocellulose blot. Other lanes were probed with the 1C2 antibody as well as the monoclonal antibodies that we had generated (1F11E5, 4H7H7, 3A2D3, 4F1B5, 3C4A6, 3B5H10). The 1C2 antibody as well as the 1F11E5, 4H7H7, 3A2D3, 4F1B5, 3C4A6 and 3B5H10 generally bound to mutant huntingtin with little if any binding to wild-type huntingtin. Although all of these antibodies showed similar specificity for mutant huntingtin, the amount of antibody required to generate a comparable signal was different. The amount of the 1C2 antibody necessary to generate a comparable western blot signal was always greater than the amount of 1F11E5, 4H7H7, 3A2D3, 4F1B5, 3C4A6 and 3B5H10 antibodies needed. In addition, some of the antibodies such as the 3B5H10 generated strong western blot signals even when similar amounts of the 1C2 antibody produced signals that were undetectable using similar detection conditions. Together, the results indicate that the 1C2 antibody binds with less affinity or less avidity than the 1F11E5, 4H7H7, 3A2D3, 4F1B5, 3C4A6 and 3B5H10 antibodies.

To further test the specificity of the 1F11E5, 4H7H7, 3A2D3, 4F1B5, 3C4A6 antibodies for mutant huntingtin compared with wild-type huntingtin and to compare their performance to the 1C2 antibody, immunoprecipitations were performed. The antibodies were screened against extracts prepared from COS cells expressing wild-type or mutant huntingtin. First, equal amounts of wild-type (480-17) and mutant huntingtin (480–68) were loaded into a tube, diluted with phosphate buffered saline, and 5 µl of monoclonal antibody were added to each tube. After 60 minutes of gentle rocking, 50 µl of a 50% protein A bead solution was added. The tubes were rocked for an additional 60 minutes and then the beads were pelleted and washed. Sample buffer was added to the beads and then subjected to SDS-PAGE and western blot analysis using the 4C8 antibody. Control lanes confirmed that approximately equal amounts of wild-type (480-17) and mutant (480-68) huntingtin were added to the tubes and an estimate of the signal generated by the secondary antibody binding to either the 1C2 or the 3B5H10 antibody used in the immunoprecipitation suggested that approximately equal amounts of 1C2 and 3B5H10 antibody had been added. Nevertheless, the 3B5H10 antibody immunoprecipitated significantly more mutant huntingtin than the 1C2 antibody whereas neither the 3B5H10 antibody nor the 1C2 antibody immunoprecipitated wild-type huntingtin. These results indicate that the antibodies that we have generated remain specific for mutant huntingtin over wild-type huntingtin, even when they are in their native conformations. This is a critical feature of the use of the antibody for drug discovery or therapeutic applications in which the target is mutant huntingtin in its native state. Furthermore, the results indicate that the 3B5H10 antibody binds with greater affinity and/or avidity to mutant huntingtin than does the 1C2 antibody.

It is evident from the above results and discussion that important new antibodies that recognize polyglutamine expansion containing proteins, such as mutant huntingtin protein, are provided. As the subject antibodies provide for improved binding properties with respect to polyglutamine expansion containing proteins such as mutant huntingtin protein as compared to known antibodies, e.g. 1C2, they subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A monoclonal antibody that recognizes a protein having a polyglutamine expansion, wherein the percentage of non-glutamine residues in said polyglutamine expansion does not exceed 10% and said antibody has greater mutant huntingtin protein binding affinity than a 1C2 monoclonal antibody.

2. The antibody according to claim 1, wherein said percentage of non-glutamine residues in said polyglutamine expansion does not exceed 5%.

3. The antibody according to claim 1, wherein said antibody binds to mutant huntingtin protein.

4. The antibody according to claim 1, wherein said antibody is produced using a fusion protein of an N-terminal fragment of a mutant human huntingtin protein.

5. A monoclonal antibody that binds to mutant huntingtin protein having a polyglutamine expansion, wherein the percentage of non-glutamine residues in said polyglutamine expansion does not exceed 10% and said antibody has greater mutant huntingtin protein binding affinity than a 1C2 monoclonal antibody.

6. The monoclonal antibody according to claim 5, wherein said antibody recognizes said polyglutamine expansion of said mutant huntingtin protein.

7. A binding fragment of an antibody according to claim 1.

8. A binding fragment of an antibody according to claim 5.

9. A cell that secretes an antibody according to claim 1.

10. The cell according to claim 9, wherein said cell is a hybridoma cell.

11. A binding fragment of an antibody that recognizes a protein having a polyglutamine expansion, wherein said binding fragment binds to said protein in a manner that differs from a 1C2 monoclonal antibody in terms of at least one of specificity, affinity and avidity for said protein.

12. The binding fragment according to claim 11, wherein said binding fragment has greater mutant huntingtin protein binding affinity than a 1C2 monoclonal antibody.

13. The binding fragment according to claim 11, wherein said binding fragment binds to mutant huntingtin protein.

14. The antibody according to claim 1, wherein said percentage of non-glutamine residues in said polyglutamine expansion does not exceed 3%.

15. The antibody according to claim 1, wherein said polyglutamine expansion is a homopolyglutamine expansion.

16. The antibody according to claim 5, wherein said percentage of non-glutamine residues in said polyglutamine expansion does not exceed 5%.

17. The antibody according to claim 5, wherein said percentage of non-glutamine residues in said polyglutamine expansion does not exceed 3%.

18. The antibody according to claim 5, wherein said polyglutamine expansion is a homopolyglutamine expansion.

19. A monoclonal antibody, or binding fragment thereof, selected from the group consisting of 1F11E5, 4H7H7, 3A2D3, 4F1B5, 3C4A6, and 3B5H10.

20. A binding fragment of an antibody according to claim 19.

21. A cell that secretes an antibody according to claim 19.

22. The cell according to claim 21, wherein said cell is a hybridoma cell.

* * * * *